US012773288B2

(12) United States Patent
Hagn et al.

(10) Patent No.: US 12,773,288 B2
(45) Date of Patent: Oct. 27, 2026

(54) SETTING REMOTE CENTER OF MOTION IN SURGICAL ROBOTIC SYSTEM

(71) Applicant: Covidien LP, Mansfield, MA (US)

(72) Inventors: Ulrich Hagn, Munich (DE); Brian A. Rockrohr, Guilford, CT (US); Ranjan Kumar Mishra, Orange, CT (US); Jaimeen V. Kapadia, Cambridge, MA (US); Rainer C. Konietschke, Wessling (DE); Paul M. Loschak, Somerville, MA (US)

(73) Assignee: Covidien LP, Mansfield, MA (US)

( * ) Notice: Subject to any disclaimer, the term of this patent is extended or adjusted under 35 U.S.C. 154(b) by 213 days.

(21) Appl. No.: 18/683,034

(22) PCT Filed: Sep. 27, 2022

(86) PCT No.: PCT/IB2022/059189

§ 371 (c)(1),
(2) Date: Feb. 12, 2024

(87) PCT Pub. No.: WO2023/052998

PCT Pub. Date: Apr. 6, 2023

(65) Prior Publication Data

US 2025/0134609 A1 May 1, 2025

Related U.S. Application Data

(60) Provisional application No. 63/250,487, filed on Sep. 30, 2021.

(51) Int. Cl.

*A61B 34/37* (2016.01)
*A61B 1/00* (2006.01)

(Continued)

(52) U.S. Cl.

CPC .......... *A61B 34/37* (2016.02); *A61B 1/00149* (2013.01); *A61B 1/04* (2013.01);

(Continued)

(58) Field of Classification Search

CPC ..... A61B 34/37; A61B 34/30; A61B 1/00149; A61B 1/04; A61B 1/3132; A61B 17/3423;

(Continued)

(56) References Cited

U.S. PATENT DOCUMENTS 6,132,368 A 10/2000 Cooper
6,206,903 B1 3/2001 Ramans (Continued)

FOREIGN PATENT DOCUMENTS

CN 113180828 A 7/2021
KR 101413406 B1 6/2014

(Continued)

OTHER PUBLICATIONS

International Search Report and Written Opinion of the International Searching Authority issued in corresponding application PCT/IB2022/059189 mailed Jan. 30, 2023 (16 pages).

*Primary Examiner* — Nhi Q Bui

(74) *Attorney, Agent, or Firm* — Carter, DeLuca & Farrell, LLP

(57) ABSTRACT

A surgical robotic system is configured to control a surgical robotic arm that conforms to the constraints of an incision point without physical constraints, such as a port latch coupling an access port to the robotic arm. The system is also configured to continuously monitor and determine the relative location of the incision point, the access port with respect to the robotic arm, and/or the instrument. Location (Continued)

and position of these components may be accomplished using cameras, electromagnetic sensors, and other tracking methodologies.

20 Claims, 8 Drawing Sheets

(51) Int. Cl.
*A61B 1/04* (2006.01)
*A61B 1/313* (2006.01)
*A61B 17/34* (2006.01)
*A61B 34/20* (2016.01)
*A61B 34/30* (2016.01)
*A61B 90/00* (2016.01)

(52) U.S. Cl.
CPC ........ *A61B 1/3132* (2013.01); *A61B 17/3423* (2013.01); *A61B 2034/2051* (2016.02); *A61B 2034/2055* (2016.02); *A61B 2034/302* (2016.02); *A61B 2090/3937* (2016.02)

(58) Field of Classification Search
CPC .... A61B 2034/2051; A61B 2034/2055; A61B 2034/302; A61B 2090/3937
See application file for complete search history.

(56) References Cited

U.S. PATENT DOCUMENTS 6,246,200 B1 6/2001 Blumenkranz et al.
6,312,435 B1 11/2001 Wallace et al.
6,331,181 B1 12/2001 Tierney et al.
6,394,998 B1 5/2002 Wallace et al.
6,424,885 B1 7/2002 Niemeyer et al.
6,441,577 B2 8/2002 Blumenkranz et al.
6,459,926 B1 10/2002 Nowlin et al.
6,491,691 B1 12/2002 Morley et al.
6,491,701 B2 12/2002 Tierney et al.
6,493,608 B1 12/2002 Niemeyer
6,565,554 B1 5/2003 Niemeyer
6,645,196 B1 11/2003 Nixon et al.
6,659,939 B2 12/2003 Moll
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.

(56) References Cited

U.S. PATENT DOCUMENTS

| | | | |
|---|---|---|---|
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,608,773 | B2 | 12/2013 | Tierney et al. |
| 8,620,473 | B2 | 12/2013 | Diolaiti et al. |
| 8,624,537 | B2 | 1/2014 | Nowlin et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |
| 8,668,638 | B2 | 3/2014 | Donhowe et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,808,164 | B2 | 8/2014 | Hoffman et al. |
| 8,816,628 | B2 | 8/2014 | Nowlin et al. |
| 8,821,480 | B2 | 9/2014 | Burbank |
| 8,823,308 | B2 | 9/2014 | Nowlin et al. |
| 8,827,989 | B2 | 9/2014 | Niemeyer |
| 8,838,270 | B2 | 9/2014 | Druke et al. |
| 8,852,174 | B2 | 10/2014 | Burbank |
| 8,858,547 | B2 | 10/2014 | Brogna |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,322,514 | B2 | 6/2019 | Vander Poorten et al. |
| 10,335,242 | B2 | 7/2019 | Devengenzo et al. |
| 10,405,934 | B2 | 9/2019 | Prisco et al. |

(56) References Cited

U.S. PATENT DOCUMENTS

| | | | |
|---|---|---|---|
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |
| 11,185,378 | B2 | 11/2021 | Weir et al. |
| 11,191,596 | B2 | 12/2021 | Thompson et al. |
| 11,197,729 | B2 | 12/2021 | Thompson et al. |
| 11,213,360 | B2 | 1/2022 | Hourtash et al. |
| 11,221,863 | B2 | 1/2022 | Azizian et al. |
| 11,234,700 | B2 | 2/2022 | Ragosta et al. |
| 11,241,274 | B2 | 2/2022 | Vaders et al. |
| 11,241,290 | B2 | 2/2022 | Waterbury et al. |
| 11,259,870 | B2 | 3/2022 | DiMaio et al. |
| 11,259,884 | B2 | 3/2022 | Burbank |
| 11,272,993 | B2 | 3/2022 | Gomez et al. |
| 11,272,994 | B2 | 3/2022 | Saraliev et al. |
| 11,291,442 | B2 | 4/2022 | Wixey et al. |
| 11,291,513 | B2 | 4/2022 | Manzo et al. |
| 11,376,002 | B2 | 7/2022 | Shelton, IV et al. |
| 11,376,098 | B2 | 7/2022 | Shelton, IV et al. |
| 11,381,759 | B2 | 7/2022 | Zhao et al. |
| 11,382,621 | B2 | 7/2022 | Scheib et al. |
| 11,382,624 | B2 | 7/2022 | Harris et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,638 | B2 | 7/2022 | Harris et al. |
| 11,382,644 | B2 | 7/2022 | Schoettgen et al. |
| 11,389,160 | B2 | 7/2022 | Shelton, IV et al. |
| 11,389,255 | B2 | 7/2022 | DiMaio et al. |
| 11,399,906 | B2 | 8/2022 | Shelton, IV et al. |
| 11,406,379 | B2 | 8/2022 | Hess et al. |
| 11,410,259 | B2 | 8/2022 | Harris et al. |
| 11,419,630 | B2 | 8/2022 | Yates et al. |
| 11,424,027 | B2 | 8/2022 | Shelton, IV |
| 11,432,888 | B2 | 9/2022 | Diolaiti et al. |
| 11,432,893 | B2 | 9/2022 | Itkowitz et al. |
| 11,432,895 | B2 | 9/2022 | Loh et al. |
| 11,439,390 | B2 | 9/2022 | Patel et al. |
| 11,439,391 | B2 | 9/2022 | Bruns et al. |
| 11,468,791 | B2 | 10/2022 | Jarc et al. |
| 11,471,155 | B2 | 10/2022 | Shelton, IV et al. |
| 11,471,221 | B2 | 10/2022 | Zhao et al. |
| 11,478,308 | B2 | 10/2022 | Hoffman et al. |
| 11,490,977 | B2 | 11/2022 | Schena et al. |
| 11,497,499 | B2 | 11/2022 | Shelton, IV et al. |
| 11,504,119 | B2 | 11/2022 | Shelton, IV et al. |
| 11,504,124 | B2 | 11/2022 | Patel et al. |
| 11,510,743 | B2 | 11/2022 | Shelton, IV et al. |
| 11,517,312 | B2 | 12/2022 | Wixey |
| 11,517,325 | B2 | 12/2022 | Shelton, IV et al. |
| 11,518,048 | B2 | 12/2022 | Saraliev et al. |
| 2016/0206387 | A1* | 7/2016 | Zhao ...................... B25J 9/1689 |
| 2019/0060019 | A1* | 2/2019 | Maret .................... A61B 34/20 |
| 2020/0038116 | A1 | 2/2020 | Toporek et al. |
| 2020/0198147 | A1* | 6/2020 | Fredrickson ........... B25J 9/0084 |
| 2020/0246085 | A1 | 8/2020 | Noonan et al. |
| 2020/0261155 | A1 | 8/2020 | Popovic et al. |
| 2021/0023719 | A1* | 1/2021 | Alt ......................... B25J 9/1697 |

FOREIGN PATENT DOCUMENTS

| | | | |
|---|---|---|---|
| WO | 2016141378 | A1 | 9/2016 |
| WO | 2021030651 | A1 | 2/2021 |
| WO | 2021252263 | A1 | 12/2021 |

* cited by examiner

SETTING REMOTE CENTER OF MOTION IN SURGICAL ROBOTIC SYSTEM

CROSS REFERENCE TO RELATED APPLICATIONS

The present application is a U.S. National Stage Application filed under 35 U.S.C. § 371(a) of International Patent Application No. PCT/IB2022/059189, filed on Sep. 27, 2022, which claims the benefit of and priority to U.S. Patent Provisional Application No. 63/250,487, filed on Sep. 30, 2021. The entire disclosures of the foregoing applications are incorporated by reference herein.

BACKGROUND

Surgical robotic systems may include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

In robot-assisted laparoscopic surgery, robotic arms are used to guide laparoscopic instruments. Such robotic arms are mounted to a stationary point, e.g., mobile carts, the operating table, a ceiling support system, etc. and are equipped with laparoscopic instruments at their end-effectors. During surgery, laparoscopic instruments are moved about the incision point (also known as fulcrum point) in the patient's body wall. This motion constraint is considered either through the kinematics design of the robotic arm inherently allowing only motion about the incision point or by commanding the robotic arm motion in a way that complies with the constraint of the incision point.

SUMMARY

The present disclosure provides for a system and method for controlling a surgical robotic arm that conforms to the constraints of an incision point without physical constraints, such as a port latch coupling an access port to the robotic arm. The system is configured to continuously monitor and determine the relative location of the incision point based on the location of the access port with respect to the robotic arm and/or the instrument.

According to one embodiment of the present disclosure, a surgical robotic system is disclosed. The surgical robotic system includes a robotic arm having a plurality of joints. The system also includes an access port disposed in a patient body wall through an incision point and decoupled from the robotic arm. The system further includes an instrument coupled to the robotic arm and configured to be inserted into the access port. The system also includes a surgeon console having a handle controller configured to receive user input for moving the instrument and the robotic arm, and a controller configured to maintain a remote center of motion which aligns with the incision point while moving at least one of the instrument or the robotic arm.

Implementations of the above embodiment may include one or more of the following features. According to one aspect of the above embodiment, the surgical robotic system may also include an instrument drive unit coupled to the robotic arm and configured to actuate the instrument. The system may also include a camera configured to capture video of the robotic arm, where the controller is configured to determine a position of at least one joint of the plurality of joints based on the video. Each joint of the plurality of joints may include a marker detectable by the camera. The system may also include an endoscope camera configured to capture video of the access port and the controller may be configured to determine a position of the access port based on the video. The access port may include a marker detectable by the endoscope camera. The surgical robotic system may further include at least one electromagnetic tracker disposed on at least one of the access port, the instrument, or the robotic arm and an electromagnetic emission detector configured to monitor electromagnetic emission of the at least one electromagnetic tracker and to determine position of the at least one electromagnetic tracker based on the electromagnetic emission. The controller may be further configured to maintain the remote center of motion based on the position of the at least one electromagnetic tracker.

According to another embodiment of the present disclosure, a surgical robotic system is disclosed. The surgical robotic system includes a robotic arm having a plurality of joints. The system also includes an access port disposed in a patient body wall through an incision point and decoupled from the robotic arm. The system further includes a controller configured to move the robotic arm to maintain a remote center of motion which aligns with the incision point.

Implementations of the above embodiment may include one or more of the following features. According to one aspect of the above embodiment, the surgical robotic system may include an instrument and an instrument drive unit coupled to the robotic arm and configured to actuate the instrument. The surgical robotic system may also include a surgeon console having a handle controller configured to receive user input for moving the instrument and the robotic arm. The controller may be further configured to maintain the remote center of motion while moving the instrument and the robotic arm. The controller may be further configured to determine a position of at least one joint of the plurality of joints based on the video. Each joint of the plurality of joints may include a marker detectable by the camera. The endoscope camera may be configured to capture video of the access port and the controller may be further configured to determine a position of the access port based on the video. The access port may include a marker detectable by the endoscope camera.

According to another embodiment of the present disclosure, a method for controlling a surgical robotic system is disclosed. The method may include receiving user input at a surgeon console having a handle controller configured to receive the user input. The method also includes moving at least one of an instrument or a robotic arm in response to the user input, where the instrument is inserted through an access port disposed in a patient body wall through an incision point and decoupled from the robotic arm, which may include a plurality of joints. The method further includes maintaining a remote center of motion which aligns with the incision point while moving at least one of the instrument or the robotic arm.

Implementations of the above embodiment may include one or more of the following features. According to one aspect of the above embodiment, the method may also include capturing video of the robotic arm at a video camera and determining a position of at least one joint of the plurality of joints based on the video. The method may further include capturing video of the access port at an endoscope camera coupled to the robotic arm and determining a position of the access port based on the video. The method may also include monitoring electromagnetic emission of at least one electromagnetic tracker disposed on at least one of the access port, the instrument, or the robotic arm; determining a position of the at least one electromagnetic tracker an electromagnetic emission detector; and determining a position of at least one of the access port, the instrument, or the robotic arm based on the position of the at least one electromagnetic tracker.

BRIEF DESCRIPTION OF THE DRAWINGS

Various embodiments of the present disclosure are described herein with reference to the drawings wherein.

DETAILED DESCRIPTION

Figure 1:
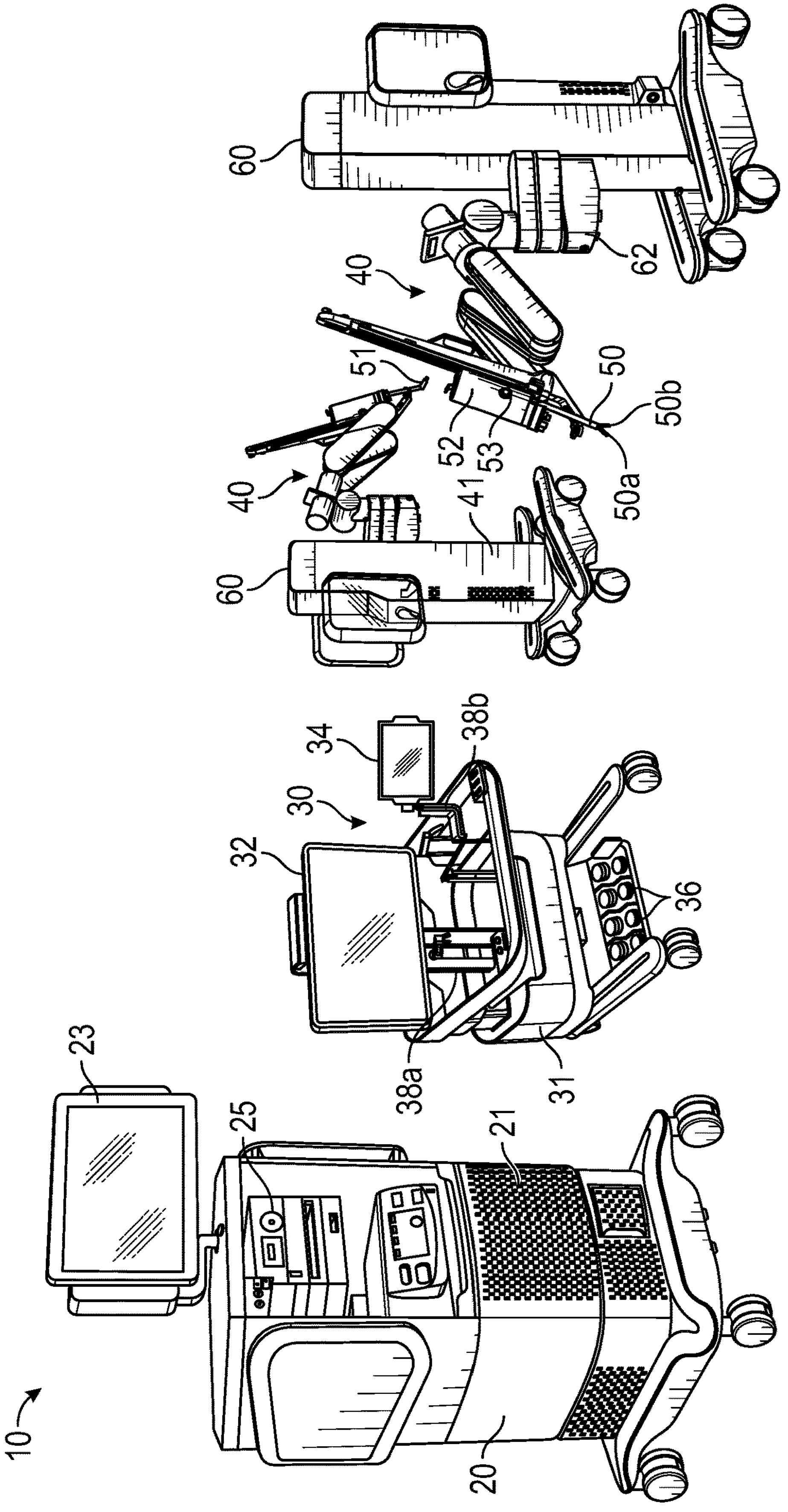
FIG. 1 is a schematic illustration of a surgical robotic system including a control tower, a console, and one or more surgical robotic arms each disposed on a movable cart according to an embodiment of the present disclosure.

Embodiments of the presently disclosed surgical robotic system are described in detail with reference to the drawings, in which like reference numerals designate identical or corresponding elements in each of the several views. As used herein the term "proximal" refers to the portion of the surgical robotic system and/or the surgical instrument coupled thereto that is closer to a base of a robot, while the term "distal" refers to the portion that is farther from the base of the robot.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more movable carts 60. Each of the movable carts 60 includes a robotic arm 40 having a surgical instrument 50 removably coupled thereto. The robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to an image processing device 56, which may be disposed within the control tower 20. The image processing device 56 may be any computing device as described below configured to receive the video feed from the endoscopic camera 51 perform the image processing based on the depth estimating algorithms of the present disclosure and output the processed video stream.

The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38*a* and 38*b* which are used by a user to remotely control robotic arms 40. The surgical console further includes an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38*a* and 38*b*.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
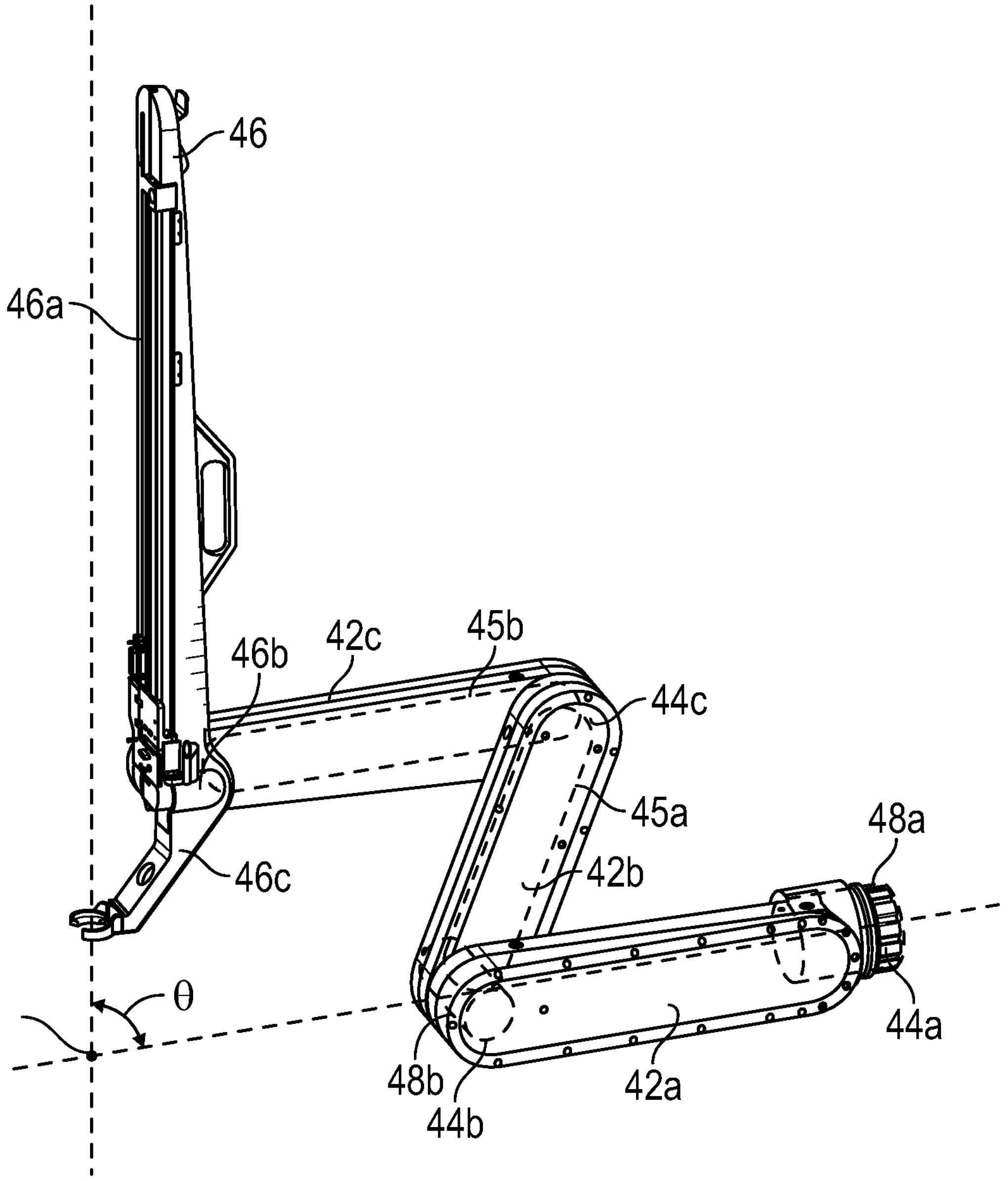
FIG. 2 is a perspective view of a surgical robotic arm of the surgical robotic system of FIG. 1 according to an embodiment of the present disclosure.
Figure 3:
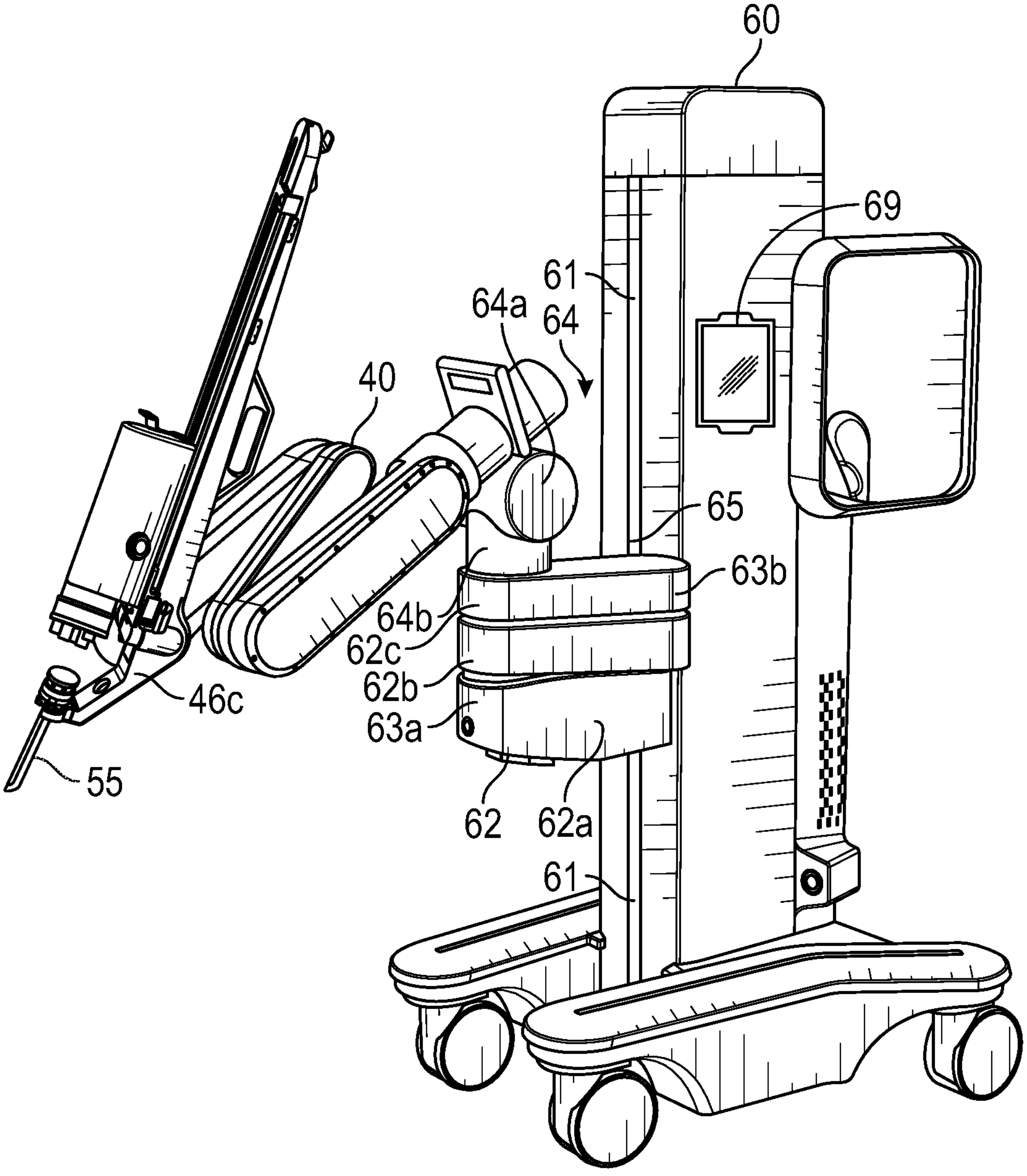
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62*a*, 62*b*, 62*c* as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and the holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. In other words, the pivot point "P" is a remote center of motion (RCM) for the robotic arm 40. Thus, the actuator 48*b* controls the angle $\theta$ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle $\theta$. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector 54) of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic access port 55 (FIG. 3) held by the holder 46 and in particular by a grasper 47. The holder 46 also includes a port latch 46*c* for securing the port 55 to the holder 46 (FIGS. 2 and 3).

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

Figure 4:
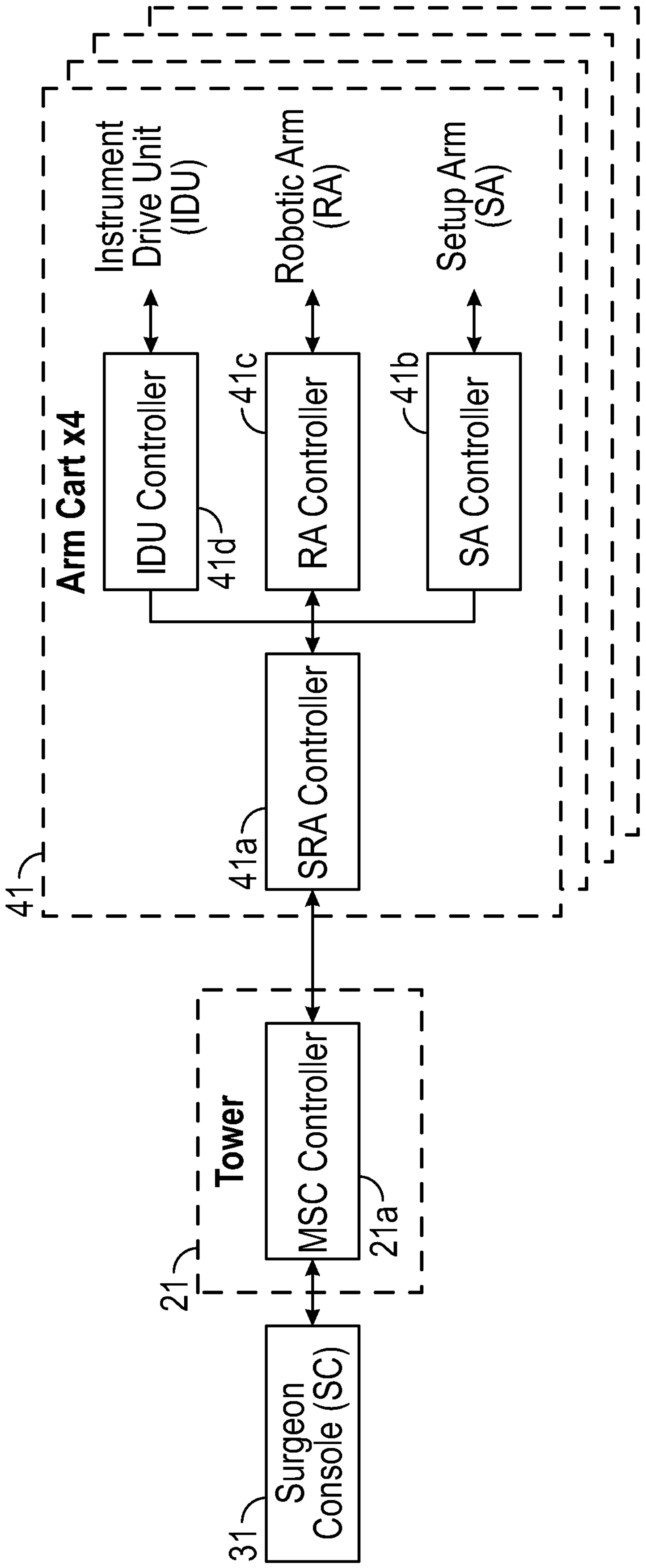
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgical console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgical console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

Each of joints 63*a* and 63*b* and the rotatable base 64 of the setup arm 62 are passive joints (i.e., no actuators are present therein) allowing for manual adjustment thereof by a user. The joints 63*a* and 63*b* and the rotatable base 64 include brakes that are disengaged by the user to configure the setup arm 62. The setup arm controller 41*b* monitors slippage of each of joints 63*a* and 63*b* and the rotatable base 64 of the setup arm 62. when brakes are engaged or can be freely moved by the operator when brakes are disengaged, but do not impact controls of other joints. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the handle controller controlling the robotic arm 40, e.g., the handle controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controller 38*a* may be embodied as a coordinate position and roll-pitch-yaw (RPY) orientation relative to a coordinate reference frame, which is fixed to the surgical console 30. The desired pose of the instrument 50 is relative to a fixed frame on the robotic arm 40. The pose of the handle controller 38*a* is then scaled by a scaling function executed by the controller 21*a*. In embodiments, the coordinate position is scaled down and the orientation is scaled up by the scaling function. In addition, the controller 21*a* also executes a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

With reference to FIGS. 5-8, a surgical robotic arm 100 is similar to the robotic arm 40 and may also be used as part of the surgical robotic system 10. The robotic arm 100 is not attached to the access port 55 via the port latch 46*c* and is controlled via the computer 21 and computer 31 to maintain the RCM. The surgical robotic arm 100 includes six (6) or more independent degrees of freedom (DoF) allowing for the robotic arm 100 to be used in minimally invasive surgical procedures and to comply with the constraints of the incision point by applying a soft RCM approach, i.e., constraining the robotic arm 100 to the RCM without mechanically coupling the access port 55 to the robotic arm 100 aside from the instrument 50 being inserted into the access port 55. Thus, the access port 55 is decoupled from the robotic arm 100, i.e., the port latch 46*c* (FIG. 3) is not in use.

The robotic arm 100 includes a plurality of joints 101, 102, 103, 104, 105, 106. Each of the joints 101, 102, 103, 104, 105, 106 provides one or more DoF, providing a total of six or more DoFs for the robotic arm 100 at its end effector 120. The joint 101 is coupled to a first link 111, which acts as a base and is configured to secure the robotic arm 100 to the movable cart 60. The first joint 101 may be configured to rotate in a plane that is transverse to a longitudinal axis defined by the first link 111. The second joint 102 is coupled to the first joint 101 via a second link 112 and may be an articulating joint. The third joint 103 is coupled to the second joint 102 via a third link 113. The third joint 103 may also be an articulating joint. The fourth joint 104 is coupled to the third joint 103 via a fourth link 114. The fourth joint 104 may be rotational joint similar to the first joint 101 such that the fourth joint 104 is configured to rotate in a plane that is transverse to a longitudinal axis defined by the fourth link 114. The fifth joint 105 is coupled to the fourth joint 104 via a fifth link 115. The fifth joint 105 may be an articulating joint. The sixth joint 106 may be a rotational joint similar to the first joint 101 and the fourth joint 104 and is coupled to the fifth joint 105 via a sixth link 116. The sixth joint 105 is an end effector of the robotic arm 100 and may include an IDU 120, which is similar to the IDU 52. The IDU 120 is configured to couple to the instrument 50 and to control and actuate the instrument 50 to perform surgical procedures. The robotic arm 100 depicts an exemplary kinematic chain and other joint configurations are contemplated, such as prismatic or multi-DoF joints.

During minimally invasive surgery motion of the instrument 50 is limited by an incision point "I" in a body wall "BW" through which the access port 55 is inserted. In particular, the incision point “I” eliminates two DoF (i.e., two translations). Therefore, in a six DoF robotic arm 100, a maximum of four DoF for the end effector disposed at a distal end portion of the instrument 50 can be achieved inside the patient body through motions of the robotic arm 100, which provides six DoF (i.e., 6−2=4). In embodiments, additional DoF can be added inside the patient by adding joints at the end effector of the instrument 50, e.g., wrist joints for a grasper.

In order to provide for soft RCM control of the robotic arm 100, the location of the incision point “I” in the patient’s body wall “BW” is determined in relation to the kinematics of the robotic arm 100, i.e., the joints 101, 102, 103, 104, 105, 106. The location of the incision point “I” may be used as an additional constraining DoF (degree of freedom) in the inverse kinematics calculations to determine a desired pose for the robotic arm 100. The inverse kinematics solution is a set of mathematical terms to derive the positions for each of the joints 101, 102, 103, 104, 105, 106 in order to move the IDU 120 to a desired pose in space.

As noted above, during minimally invasive surgery the motion of the instrument 50 is limited by the incision point “I”, which eliminates two DoF (i.e., two translations). The incision point “I” may not be an ideal point and its location in the body wall is selected by the clinician based on clinical outcome, e.g., targeted to have as low trauma as possible, rather than ease of movement for the robotic arm 100. Typically, the access port 55, which acts as a pressure seal to contain the insufflation of the body cavity, is placed at the incision and the access port includes a depth port marker 57, which may be a ring or any other fiducial marker disposed on the outside surface of the tube. During insertion of the access port 55, the port marker 57 that is lined up by the clinician with the proposed incision point “I”. The access port 55 is inserted to a depth at which the port marker 57 aligns with the desired incision point “I”. The access port 55 may also include a top port marker 58, which may have a ring shape and is disposed on a top surface of the access port 55 through which the instrument 50 is inserted.

Figure 7:
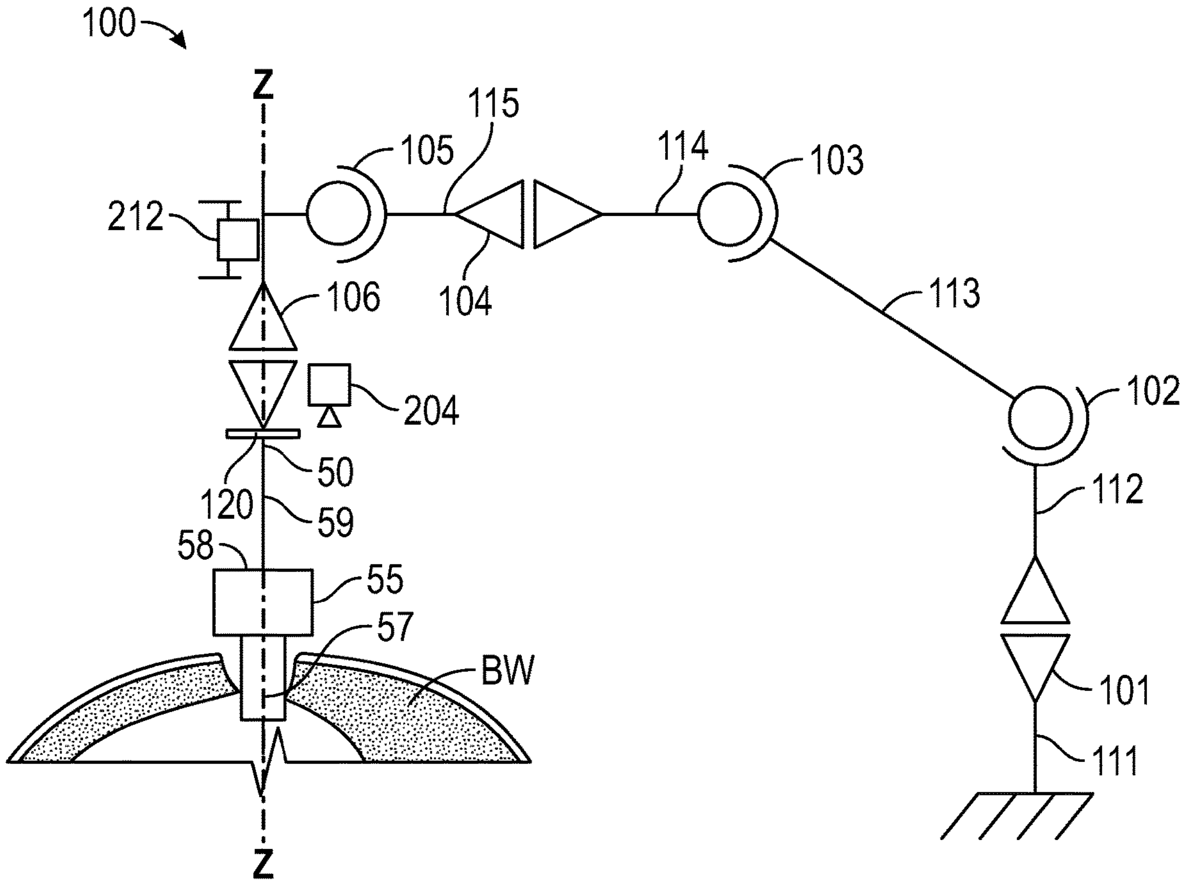
FIG. 7 is a schematic diagram of the surgical robotic arm of FIG. 6 with the surgical instrument inserted into the access port according to one embodiment of the present disclosure.

Since the location of the access port 55 coincides to the location of the incision point “I”, knowing the location of the port marker 57 with respect to the kinematics of the robotic arm 100 allows for implementing the limitation in the inverse kinematics such that the motion of the robotic arm 100 is controlled in a way that a longitudinal axis “Z-Z” defined by the instrument 50 always intersects with the incision point “I” (FIG. 7). If the incision point “I” does not change its location during surgery, it is feasible to identify the location of the incision point “I” once in relation to the robotic arm 100 and keep the incision point “I” static. In case the incision point “I” moves (e.g., due to bed and/or patient adjustment), the location of the incision point needs to be updated (i.e., dynamic position).

The surgical robotic system 10 is configured to identify the transformation between the robotic arm 100, and the incision point “I” and use that transformation to control the movement of the robotic arm 100. To aide in tracking of the instrument 50 an instrument marker 59 may be disposed anywhere on the instrument 50, e.g., longitudinal shaft. The instrument marker 59 may be a ring or any other suitable fiducial marker. Prior to coupling the instrument 50 to the IDU 120, the transformation of the robotic arm 100 may be calculated on the position of the base, i.e., the first link 111 and/or of the end effector of the robotic arm 100, i.e., the IDU 120. Once the instrument 50 is coupled to the IDU 120, then the transformation may be calculated on the position of the instrument marker 59 on the instrument 50 and/or the end effector 54 of the instrument 50. The position of the incision point “I” may be determined based on a position of the port marker 57 and/or the top marker 58 of the access port.

Figure 9:
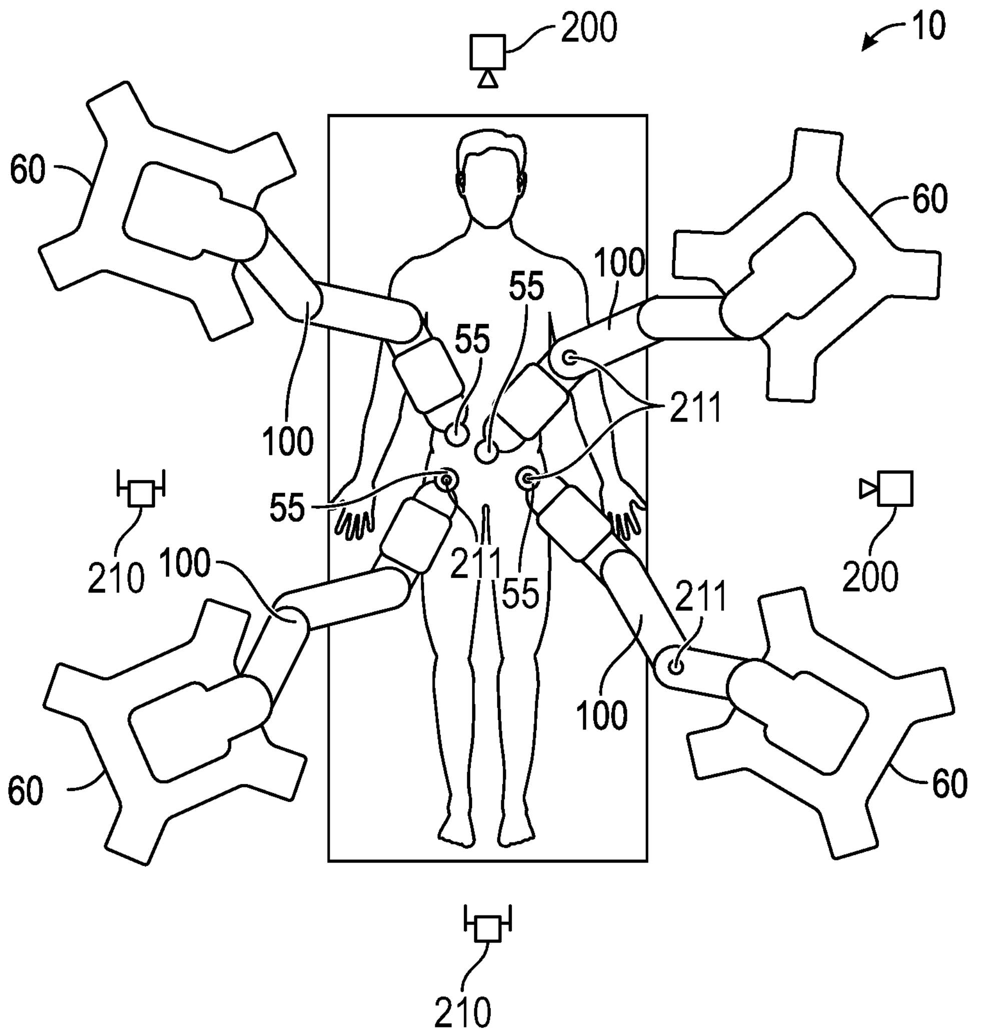
FIG. 9 is a plan schematic view of movable carts of FIG. 1 with robotic arms of FIG. 6 positioned about a surgical table according to an embodiment of the present disclosure.

With reference to FIG. 9, the surgical robotic system 10 is setup around the surgical table 200 in an operating room “OR”. The system 10 includes movable carts 60. The movable carts 60 may be positioned relative to the surgical table 200 and each other using any suitable registration system or method. Position and orientation of the carts 60 depend on a plurality of factors, such as placement of a plurality of ports 55, which in turn, depends on the procedure being performed. Once the port placement is determined, the access ports 55 are inserted into the patient, and carts 60 are positioned to insert instruments 50 and the endoscopic camera 51 into corresponding access ports 55. Orientation of the carts 60 and their corresponding robotic arms 100 may be based on individual laser alignment patterns. For a more detailed description of using alignment patterns to orient a plurality of movable carts 60 see International Application No. PCT/US2021/034125, titled “SURGICAL ROBOTIC SYSTEM USER INTERFACES”, filed on May 26, 2021, the entire disclosure of which is incorporated by reference herein.

The system 10 includes one or more external cameras 202 disposed anywhere around the OR with a field of view capturing each of the movable carts 60, the robotic arms 100, the access ports 55, instruments 50, etc. The external cameras 202 capture position and orientation of various components of the system 10. In addition to the port markers 57 and 58 and the instrument marker 59, the robotic arm 100 may include one or more arm markers 150*a* . . . *n* disposed on any of the joints 101, 102, 103, 104, 105, 106 or connecting links. The arm markers 150*a* . . . *n* may have any suitable shape and color and are detectable by the camera 202. The markers 57, 58, 59, and 150*a* . . . *n* may aide in identification of various components of the system 10 but are not necessary and image processing techniques may be used in lieu of or in conjunction with the markers 57, 58, 59, and 150*a* . . . *n*.

The system 10 also includes one or more external radio frequency (RF) emission detectors 210 configured to detect location and/or distance of a plurality of trackers 211, which may be disposed on the access port 55, the instrument 50, and the robotic arm 100, and in particular, on any of the joints 101, 102, 103, 104, 105, 106. Trackers 211 may be either active or passive transmitters capable of emitting electromagnetic energy detectable by the RF detectors 210, which may operate using any suitable electromagnetic spectrum transmissions configured to determine location of the trackers 211 using time of flight, triangulation, and other methods. The external cameras 202 and the RF detectors 210 are communicatively coupled to the computer 21, which is configured to process the image data from the external cameras 202 and the electromagnetic location data from the RF detectors 210 to determine position and/or orientation of the robotic arm 100, the access port 55, and the instrument 50. Image data may include image processing and detection of the access port 55, the instrument 50, and the robotic arm 100 with or without the corresponding markers 57, 58, 59, and 150*a* . . . *n* based on the shape of the objects and their known shape profiles and geometries.

The system 10 is configured to locate each of the access ports 55 and the robotic arms 100. The markers 58 and 150*a* . . . *n* may be unique to the access port 55 and the robotic arm 100 on which they are disposed, allowing the system 10 to identify the specific access port 55 and the robotic arm 100. In embodiments, the markers 150*a* . . . *n* may be unique to each of the joints 101, 102, 103, 104, 105, 106. In further embodiments, the access ports 55 and the robotic arm 100 may include any other visual identifier, such as numeric, alphanumeric, or pictograms that uniquely identify these components.

In addition, the system 10, and in particular, the computer 21 is configured to determine the geometry of access ports 55, namely, position, and orientation of the access port 55 including its longitudinal axis and existing features of the robotic arms 100 and computes their transformations based on the image data provided by the external cameras 202. In embodiments, the markers 57, 58, 59, and 150*a* . . . *n* may be included as part of the image data allowing the computer 21 to compute transformations of the robotic arms 100. In additional embodiments, the electromagnetic location data may be used in conjunction with or alone to determine transformations of the robotic arms 100.

With reference to FIGS. 5-8, a surgical robotic arm 100 is similar to the robotic arm 40 and may be used as part of the surgical robotic system 10. The robotic arm 100 is decoupled from, i.e., not attached to the access port 55 via the port latch 46*c* or any other securing apparatus, and is controlled via the computer 21 and/or computer 31 to maintain the RCM. The surgical robotic arm 100 includes six (6) or more independent degrees of freedom (DoF) allowing for the robotic arm 100 to be used in minimally invasive surgical procedures and to comply with the constraints of the incision point by applying a soft RCM approach, i.e., constraining the robotic arm 100 to the RCM without mechanically coupling the access port 55 to the robotic arm.

With reference to FIGS. 5-8, the robotic arm 100 includes a plurality of joints 101, 102, 103, 104, 105, 106. Each of the joints 101, 102, 103, 104, 105, 106 provides one or more DoF, providing a total of six or more DoFs for the robotic arm 100 at its end effector 120. The joint 101 is coupled to a first link 111, which acts as a base and is configured to secure the robotic arm 100 to the movable cart 60. The first joint 101 may be configured to rotate in a plane that is transverse to a longitudinal axis defined by the first link 111. The second joint 102 is coupled to the first joint 101 via a second link 112 and may be an articulating joint. The third joint 103 is coupled to the second joint 102 via a third link 113. The third joint 103 may also be an articulating joint. The fourth joint 104 is coupled to the third link 113 via a fourth link 114. The fourth joint 104 may be rotational joint similar to the first joint 101 such that the fourth joint 104 is configured to rotate in a plane that is transverse to a longitudinal axis defined by the fourth link 114. The fifth joint 105 is coupled to the fourth joint 104 via a fifth link 115. The fifth joint 105 may be an articulating joint. The sixth joint 106 may be a rotational joint similar to the first joint 101 and the fourth joint 104 and is coupled to the fifth joint 105 via a sixth link 116. The sixth joint 105 includes an end effector of the robotic arm 100, which may be an IDU 120 that is similar to the IDU 52. The IDU 120 is configured to couple to the instrument 50 and to control and actuate the instrument 50 to perform surgical procedures. The robotic arm 100 depicts an exemplary kinematic chain and other joint configurations are contemplated, such as prismatic or multi-DoF joints.

Figure 8:
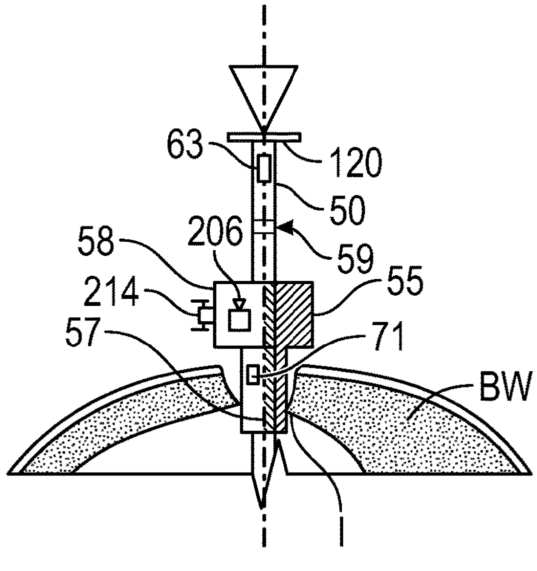
FIG. 8 is a schematic diagram of the surgical instrument inserted into the access port according to one embodiment of the present disclosure.

As shown in FIG. 8, during minimally invasive surgery motion of the instrument 50 is limited by an incision point "I" in a body wall "BW" through which the access port 55 is inserted. In particular, the incision point "I" eliminates two DoF (i.e., two translations). Therefore, in a six DoF robotic arm 100, a maximum of four DoF for the end effector disposed at a distal end portion of the instrument 50 can be achieved inside the patient body through motions of the robotic arm 100, which provides six DoF (i.e., 6−2=4). In embodiments, additional DoF can be added inside the patient by adding joints at the end effector of the instrument 50, e.g., wrist joints for a grasper.

In order to provide for soft RCM control of the robotic arm 100, the location of the incision point "I" in the patient's body wall "BW" is determined in relation to the kinematics of the robotic arm 100, i.e., the joints 101, 102, 103, 104, 105, 106. The location of the incision point "I" may be used as an additional constraining DoF (degree of freedom) in the inverse kinematics calculations to determine a desired pose for the robotic arm 100. The inverse kinematics solution is a set of mathematical terms to derive the positions for each of the joints 101, 102, 103, 104, 105, 106 in order to move the IDU 120 to a desired pose in space.

As noted above, during minimally invasive surgery the motion of the instrument 50 is limited by the incision point "I", which eliminates two DoF (i.e., two translations). The incision point "I" may not be an ideal point and its location in the body wall is selected by the clinician based on a desired clinical outcome, e.g., targeted to have as low trauma as possible, rather than ease of movement for the robotic arm 100. Typically, the access port 55, which acts as a pressure seal to contain the insufflation of the body cavity, is placed at the incision and the access port includes a depth port marker 57, which may be a ring or any other fiducial marker disposed on the outside surface of the tube. During insertion of the access port 55, the port marker 57 that is lined up by the clinician with the proposed incision point "I". The access port 55 is inserted to a depth at which the port marker 57 aligns with the desired incision point "I". The access port 55 may also include a top port marker 58, which may have a ring shape and is disposed on a top surface of the access port 55 through which the instrument 50 is inserted.

Since the location of the access port 55 coincides to the location of the incision point "I", knowing the location of the port marker 57 with respect to the kinematics of the robotic arm 100 allows for implementing the limitation in the inverse kinematics such that the motion of the robotic arm 100 is controlled in a way that a longitudinal axis "Z-Z" defined by the instrument 50 always intersects with the incision point "I" (FIG. 7). If the incision point "I" does not change its location during surgery, it is feasible to identify the location of the incision point "I" once in relation to the robotic arm 100 and keep the incision point "I" static. In case the incision point "I" moves (e.g., due to bed and/or patient adjustment), the location of the incision point needs to be updated (i.e., dynamic position).

The surgical robotic system 10 is configured to identify the transformation between the robotic arm 100, and the incision point "I" and use that transformation to control the movement of the robotic arm 100. To aide in tracking of the instrument 50 an instrument marker 59 may be disposed anywhere on the instrument 50, e.g., longitudinal shaft. The instrument marker 59 may be a ring or any other suitable fiducial marker. Prior to coupling the instrument 50 to the IDU 120, the transformation of the robotic arm 100 may be calculated on the position of the base, i.e., the first link 111 and/or of the end effector of the robotic arm 100, i.e., the IDU 120. Once the instrument 50 is coupled to the IDU 120, then the transformation may be calculated on the position of the instrument marker 59 on the instrument 50 and/or the end effector 54 of the instrument 50. The position of the incision point "I" may be determined based on a position of the port marker 57 and/or the top marker 58 of the access port.

With reference to FIG. 9, the surgical robotic system 10 is setup around the surgical table 200 in an operating room "OR". The system 10 includes movable carts 60. The movable carts 60 may be positioned relative to the surgical table 200 and each other using any suitable registration system or method. Position and orientation of the carts 60 depends on a plurality of factors, such as placement of a plurality of ports 55, which in turn, depends on the procedure being performed. Once the port placement is determined, the access ports 55 are inserted into the patient, and carts 60 are positioned to insert instruments 50 and the endoscopic camera 51 into corresponding access ports 55. Orientation of the carts 60 and their corresponding robotic arms 100 may be based on individual laser alignment patterns. For a more detailed description of using alignment patterns to orient a plurality of movable carts 60 see International Application No. PCT/US2021/034125, titled "SURGICAL ROBOTIC SYSTEM USER INTERFACES", filed on May 26, 2021, the entire disclosure of which is incorporated by reference herein.

With reference to FIG. 9, the system 10 also includes one or more external electromagnetic (e.g., radio frequency (RF)) emission detectors 210 configured to detect location and/or distance of a plurality of trackers 211, which may be disposed on the access port 55, the instrument 50, and the robotic arm 100, and in particular, on any of the joints 101, 102, 103, 104, 105, 106. Trackers 211 may be either active or passive transmitters capable of emitting electromagnetic energy detectable by the RF detectors 210, which may operate using any suitable electromagnetic spectrum transmissions configured to determine location of the trackers 211 using time of flight, triangulation, and other methods. The external cameras 202 and the RF detectors 210 are communicatively coupled to the computer 21, which is configured to process the image data from the external cameras 202 and the electromagnetic location data from the RF detectors 210 to determine position and/or orientation of the robotic arm 100, the access port 55, and the instrument 50. Image data may include image processing and detection of the access port 55, the instrument 50, and the robotic arm 100 with or without the corresponding markers 57, 58, 59, and 150*a* . . . *n* based on the shape of the objects and their known shape profiles and geometries.

The system 10 is configured to locate each of the access ports 55 and the robotic arms 100. The markers 58 and 150*a* . . . *n* may be unique to the access port 55 and the robotic arm 100 on which they are disposed, allowing the system 10 to identify the specific access port 55 and the robotic arm 100. In embodiments, the markers 150*a* . . . *n* may be unique to each of the joints 101, 102, 103, 104, 105, 106. In further embodiments, the access ports 55 and the robotic arm 100 may include any other visual identifier, such as numeric, alphanumeric, or pictograms that uniquely identify these components.

In addition, the system 10, and in particular, the computer 21 is configured to determine the geometry of access ports 55, namely, position, and orientation of the access port 55 including its longitudinal axis and existing features of the robotic arms 100 and computes their transformations based on the image data provided by the external cameras 202. In embodiments, the markers 57, 58, 59, and 150*a* . . . *n* may be included as part of the image data allowing the computer 21 to compute transformations of the robotic arms 100. In additional embodiments, the electromagnetic location data may be used in conjunction with or alone to determine transformations of the robotic arms 100.

Figure 5:
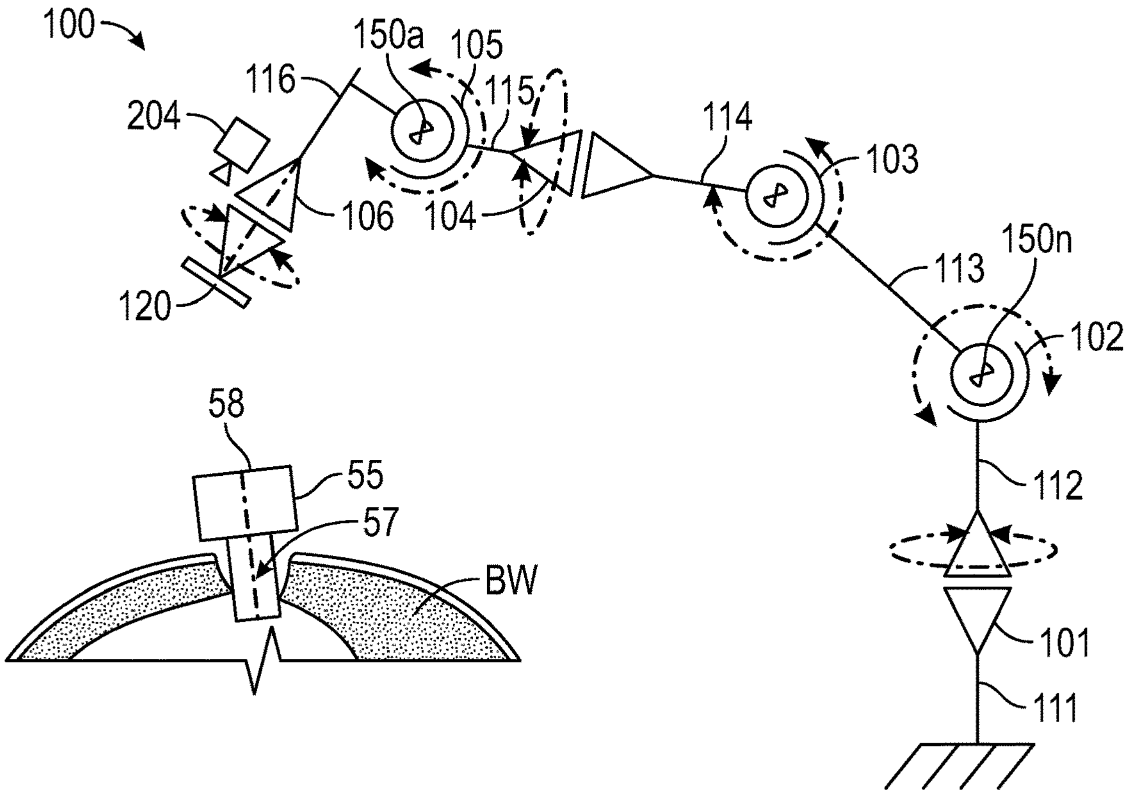
FIG. 5 is a schematic diagram of a surgical robotic arm and an access port according to one embodiment of the present disclosure.
Figure 6:
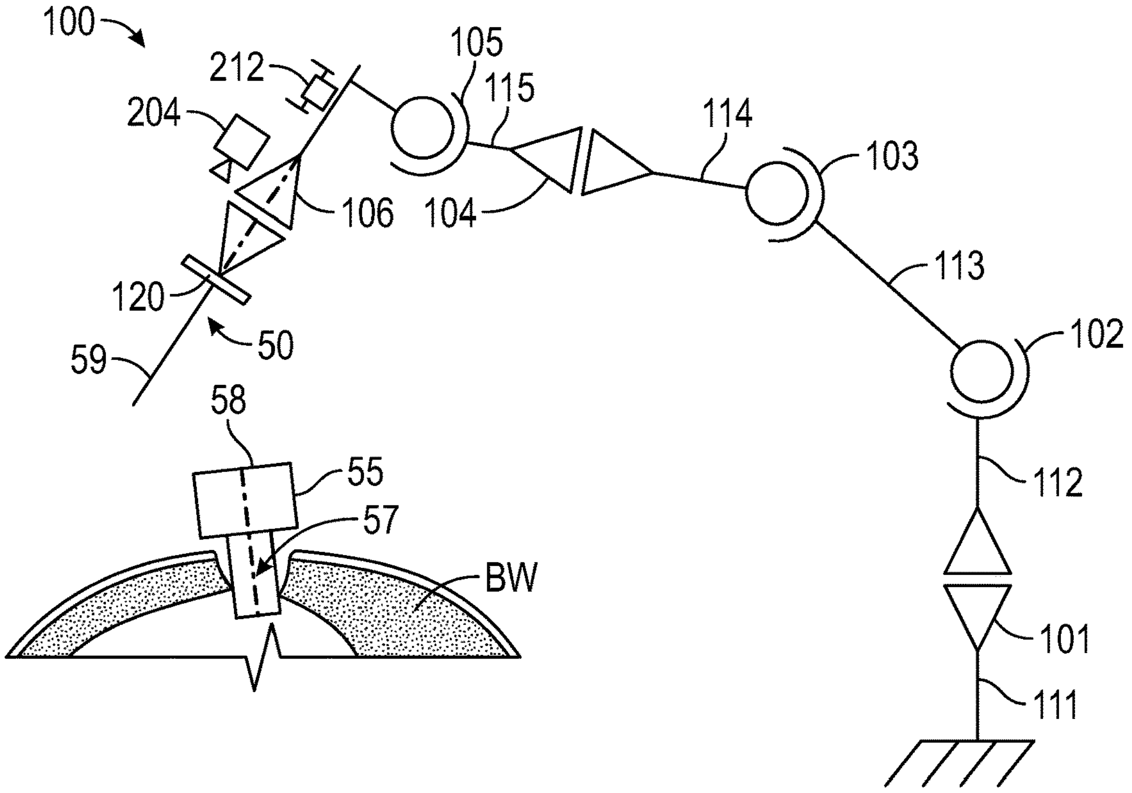
FIG. 6 is a schematic diagram of the surgical robotic arm of FIG. 5 with a surgical instrument attached thereto according to one embodiment of the present disclosure.

With reference to FIGS. 5-7, each of the robotic arms 100 may also include one or more arm cameras 204 disposed on the robotic arm 100 and/or the movable cart 60 allowing for visualization of the robotic arm 100 and the instrument 50 attached thereto. The cameras 204 may be disposed adjacent the IDU 120 allowing for an unobstructed view of the access port 55. In addition, each of the robotic arms 100 further includes one or more arm RF detectors 212 configured to detect location and/or distance of a plurality of trackers 211. The arm RF detectors 212 may be integrated at various locations of the robotic arms 100 (e.g., from the end-effector down to the base).

The arm cameras 204 and the RF detectors 212 may be communicatively coupled to the computer 21 and/or the computer 31, allowing for local processing for image and electromagnetic location data from the cameras 204 and the arm RF detectors 212. In particular, the image data may be used to identify the location of access ports 55 via the top marker 58 and one or more of the robotic arms 100 visible through the arm camera 204. The computers 21 and/or 31 may then compute relative transformation of each of the robotic arms 100 based on existing features on the robotic arms 100 (e.g., joint placement), the markers 105*a* . . . *n*, and/or trackers 211.

With reference to FIG. 8, each of the access ports 55 may also include one or more port cameras 206 disposed on the access ports 55 allowing for visualization of the robotic arms 100 and the instruments 50 attached thereto. The cameras 206 may be disposed adjacent a top surface of the access ports 55 and may be facing in an opposite direction from the insertion point allowing for an unobstructed view of the robotic arms 100 and the instruments 50. In addition, each of the access ports 55 may further include one or more port RF detectors 214 configured to detect location and/or distance of a plurality of trackers 211. The port RF detectors 214 may be integrated at various locations of the access port (e.g., at the top thereof).

The port cameras 206 and the RF detectors 214 may be communicatively coupled to the computer 21 and/or the computer 31, allowing for local processing for image and electromagnetic location data from the cameras 206 and the port RF detectors 214. In particular, the image data may be used to identify the location of the robotic arms 100 visible through the port camera 206. The computers 21 and/or 31 may then compute relative transformation of each of the robotic arms 100 based on existing features on the robotic arms 100 (e.g., joint placement), the markers 105*a* . . . *n*, and/or trackers 211.

The system 10 utilizes positional feedback external cameras 202 and/or the RF detectors 210 during each phase of movement of the robotic arm 100 as shown in FIGS. 5-8. In particular, FIG. 5 shows the robotic arm 100 during a first phase, before the instrument 50 is attached to the robotic arm 100 while the access port 55 is already placed in the body wall "BW" of the patient. FIG. 6, shows the robotic arm 100 after the instrument 50 is attached to the IDU 120. FIGS. 7 and 8 depicts the configuration of the robotic arm 100 when the instrument 50 is inserted through the port 55.

During the first phase, each of the robotic arms 100 may be manually positioned by a user by placing the robotic arm 100 in a passive mode by pressing the button 53. While the robotic arm 100 is a manual mode, the robotic arm 100 may be approximated to contact a corresponding port 55. This allows the computer 21 to recognize the position and orientation of the access port 55 by using the robotic arm 100 as a measuring device through computed kinematics.

In embodiments, the end effector of the robotic arm 100 and the access port 55 may include mating geometries (e.g., pin and socket) to confirm physical contact of the robotic arm 100 with the access port 55. Once contact is made, the user may confirm contact through a graphical user interface displayed on any of the displays 23, 32, and 34 of the system 10. In embodiments, the robotic arm 100 may include a user interface (not shown) configured to display a GUI to accomplish various tasks such as identify the location of the access port 55. The interface may be a touchscreen, a laser alignment module, a joystick, or other directional input, or a terminal for communicating port coordinates.

Furthermore, various sensors, such as contact (e.g., mechanical switch, electrical contacts) or contactless sensors (e.g., Hall effect, proximity, etc.) may be used to automatically sense when the robotic arm 100 has reached the access port 55. This allows for automatic confirmation that the robotic arm 100 and the access port 55 have made contact.

With reference to FIG. 8, the access port 55 may also include one or more sensors 71, which may be a position sensor, such as a gyroscope, accelerometer, ultra-wideband (UWB) radar, a magnetic sensor, inertial measurement unit and the like. The position sensor is configured to provide accurate location finding without line-of-sight. The sensor 71 may also be a dielectric sensor, a force sensor (e.g., strain gauge), or an optical sensor that is configured to detect incisions formed in the body wall "BW" and lateral force measurement by detecting deflection or flexure of the access port 55.

In the second phase, at least one access port 55 is inserted into the body wall "BW" and one or multiple robotic arms 100 are equipped with instruments 50 and the camera 51 without being inserted into the access port 55 as shown in FIG. 6. In this phase, the joints 101, 102, 103, 104, 105, 106 of each of the robotic arm 100 can be manipulated through manual mode. Thus, all of the above-described embodiments pertaining to the first phase may be also implemented in the second phase as well.

Since the camera 51 is attached to one of the robotic arms 100, the camera 51 may be used as an arm camera 204 to detect location, dimensions, distances, etc. of the inserted access ports 55 as well as the location of the other robotic arms 100. This data may be passed to the computers 21 and/or 31 to compute the relative transformations of the robotic arms 100. This may be done automatically right before inserting the camera 51 once all of the access ports 55 are setup and within view of the camera 51. Once inserted, the images captured inside the patient may be used to detect the shafts of instruments 50. The controller 21*a* may extract location data from the images of the access ports 55 and the inserted instruments 50 to calculate relative position of the access ports 55 to each other.

The access port 55 may be transparent, thus when inserting the camera 51, the image processing device 56 may process the video feed to analyze the images to detect the start of the patient body and the end point when the camera 51 clears the peritoneum. The access port 55 may also include distance markers disposed within the access port 55, such that as the camera 51 is inserted, distance markers may be used to determine insertion depth and compute position of camera 51 within the access port 55 by the image processing device 56.

If the access port 55 is opaque, the image processing device 56 may use the video feed to monitor the start and the end of the access port 55 during insertion. The controller 21*a* may then determine port placement and estimate the RCM based on image processing of the insertion video.

Similar to using contact sensing between the robotic arm 100 and the access port 55 during phase, each of the robotic arms 100 may use the instrument 50 attached thereto to contact a corresponding access port 55. This allows the computer 21 to recognize the position and orientation of the access port 55 by using the robotic arm 100 as a measuring device. Similar to the above-described contact sensing embodiment, mating geometries and sensors may be used to detect contact.

The IDU 120 may measure forces imparted on the instrument 50. In particular, the IDU 120 may measure the force during insertion of the instrument 50 into the access port 55. During insertion, higher friction is caused by the port seal of the access port 55, the IDU 120 utilize this detected force to automatically identify when the instrument 50 passes this depth and then utilize adherence to the access port 55 to calculate the RCM. IDU 120 may measure the forces and determinations may be performed bay of the computers 21 and/or 31 of the system 10. In addition, pressure sensors may be used to measure insufflation pressure through the access port 55 and detect drops in the pressure signal when instrument 50 is passing through the insufflation seal of the access port 55 to determine the RCM.

During the third phase, the robotic arms 100 are equipped with instruments 50 that are already partially inserted into the access ports 55 as shown in FIG. 7. During the phase, only one dimension is unknown, namely the distance between the top of the access port 55 and the end effector portion of the robotic arm 100.

The instrument marker 59 on the instrument 50, e.g., on a longitudinal shaft of the instrument 50, may be used to detect that instrument 50 has been inserted into the access port 55 to the proper depth. Any of the cameras 202, 204, 206 may be used to detect the instrument marker 59. Once proper insertion is detected based on alignment of the instrument marker 59 with the top of the access port 55 the user may confirm via a user interface that the instrument has been properly inserted. Because the instrument marker 59 has a fixed relation to the kinematics of the robotic arm 100 and the top of the access port 55 has a fixed relation to the incision point "I", the relation between the incision point "I" and the robot kinematics is identified by the controller 21*a* and may be used further on to apply the soft-RCM approach.

In embodiments, the instrument marker 59 may be removable, e.g., an elastic band, a clip, and the like. The marker 59 is configured to prevent further insertion of the instrument 50 into the access port 55 until the instrument marker is removed. The user moves the robotic arm 100 so that the instrument marker 59 contacts the top of the access port 55 like a mechanical end-stop. After confirming through user input and removing the instrument marker 59, the relation between the incision point "I" and the kinematics of the robotic arm 100 is identified and can be used further on to apply the soft-RCM approach.

The robotic arm 100 may also include a distance sensor 110, which may be a contact-less optical (e.g., laser) distance sensor or an ultrasonic distance sensor. The distance sensor 110 is configured to measure the distance between the end-effector of the robotic arm 100 (i.e., the IDU 120) and the top of the access port 55. Such optical sensor can be e.g., a laser sensor using time of flight, triangulation, and other measurement techniques.

In embodiments, the instrument marker 59 may include one or more Hall effect sensors or other magneto-sensitive sensors and the access port 55 may include permanent magnet targets. By inserting the instrument 50, as the instrument marker 59 passes the permanent magnet of the access port 55, the relation between access port 55 and instrument 50 as well as the IDU 120 is identified and can be used for the soft-RCM approach. Additional magnetic sensor instrument marker 59 may be used to update the positional relationship as the instrument 50 is moved through the access port 55.

In further embodiments, the instrument marker 59 may include a permanent magnet or magnetic linear grating and the access port 55 may include Hall effect or any other suitable magneto-sensitive sensor. Detecting the instrument marker 59 during insertion of the instrument 50 allows for establishing the relation between access port 55 and instrument 50 as well as the IDU 120 is identified and can be used for the soft-RCM approach. The instrument marker 59 may be magnetic grating including a plurality of magnets allowing for counting of the passing magnets and establishing a dynamic continuous measurement based on the same.

With reference to FIG. 8, the instrument 50 may include a distance sensor 63, which may be a cable potentiometer having one end that is couplable to the access port 55. A cable potentiometer may include a spring-loaded pulley with a cable spool and a potentiometer measuring the pulley rotations. By attaching the free end of the cable to the access port 55, the distance may be measured by reading out the potentiometer signal at the IDU controller 41*d*. Alternatively, the distance sensor 63 may be a rotary position sensor (e.g., Hall effect sensor, encoder, etc.).

In further embodiments, the distance sensor 63 may be a passive linear slide or a telescoping beam that is spring-loaded (i.e., spring-biased beam or slide in the direction of the access port 55) extending between the IDU 52 and the top of access port 55. The spring ensures that the tip of the beam or slide is pushed against the top surface of the access port 55. By measuring the position of the beam or slide, the distance between IDU 52 and the top of the access port 55 may be measured and may be used for the soft-RCM approach.

During change of the instrument 50, the robotic arm 100 may be switched into an instrument change mode during which two or more of the joints are controlled to zero torque (e.g., joints 104 and 105) to act as passive joints and the rest of the joints are commanded to move. The incision point "I" acts like a bearing constraining the motion of the robotic arm 100. The position read-out of the passive joints 104 and 105 allows for computing the distance between IDU 120 of the robotic arm 100 and the incision point "I".

In embodiments where the instrument 50 includes a pair of jaws 50*a* and 50*b* (FIG. 1), e.g., vessel sealer, grasper, scissors, etc., the jaws 50*a* and 50*b* may be used to determine the length of the access port 55 and to calculate the RCM. The jaws 50*a* and 50*b* may be biased to an open position and the torque on the actuator, i.e., the IDU 120, may be used to measure when the jaws 50*a* and 50*b* spring open to measure the insertion depth at the distal end of the access port 55. The distance traveled, namely, at which the jaws 50*a* and 50*b* sprung open are used to calculate the RCM. Similarly, the jaws 50*a* and 50*b* may be closed but may be articulated to a side to apply pressure during travel through the access port 55 and once the jaws 55*a* and 55*b*.

In embodiments, the access port 55 may include a plurality of steps within the lumen of the access port 55. The steps may vary in diameter, which may increase in diameter from an initial small diameter at the entry and smaller diameter at entry and exit of port, with a larger diameter in between. When introducing the instrument 50 the robotic arm 100 may advance the instrument 50 using a step-finding process. This process includes opening the jaws 50*a* and 50*b* such that they are in contact with the port wall. Then advancing the instrument 50 inside the access port 55 until the jaws 50*a* and 50*b* hit the step towards the smaller diameter. In further embodiments, rather than vary the inner diameter of the access port 55 in step-like increments, the inner diameter may change gradually and position of the jaws 50*a* and 50*b*, i.e., opening angle, may be used to measure the change in diameter while moving into the patient. The change in diameter is then used to determine the travel distance and RCM.

In further embodiments, position of the access port 55 may be determined during the surgical procedure as the instrument 50 is being moved by the robotic arm 100. Initially, the system 10 is provided with a default location of the instrument 50 relative to the access port 55, e.g., mid-point. As the instrument 50 is moved by the robotic arm 100 through the access port 55, torque sensing may be used to gradually refine estimation of the position of the access port 55 by monitoring the torque and minimizing calculated forces against the body wall "BW". As noted above, the sensor 71 of the access port 55 may be a force sensor configured to measure the forces applied by the access port 55 against the body wall "BW". This data may then be used during surgery to minimize such forces on the body wall "BW".

In another embodiment, the robotic arm 100 may be manually controlled to rotate the IDU 120 in a cone shape around the intended RCM. The RCM may then be calculated using the sensors, cameras, and other devices described above. In particular, any or all of the following data may be used to determine RCM: position sensing data from the robotic arm 100; force and/or torque sensing data from the robotic arm 100; or endoscope camera view from the camera 51 of the tip motion of the instrument 50 inside the patient.

Figure 10:
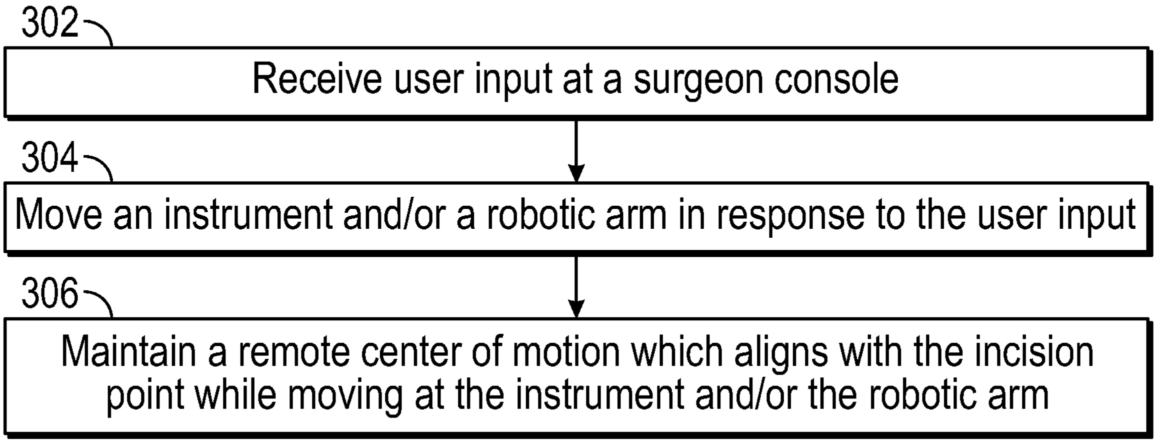
FIG. 10 is a flow chart of a method for controlling the surgical robotic arm of FIG. 6.

With reference to FIG. 10, a method for controlling the robotic arm 100 includes receiving user input at the surgeon console 30 at step 302, by moving one or both of the handle controllers 38*a* and 38*b*. As described above with respect to inverse kinematics, the user input is translated into movement commands at step 304, which move and/or actuate the instrument 50 and the robotic arm 100. The inverse kinematic calculations are performed based on the position and/or orientation of the robotic arm 100, the access port 55, the instrument 55, which may be determined using any of the visual, electromagnetic, and other tracking methods described in the present disclosure. At step 306 the RCM is maintained which aligns with the incision point "I" while moving the instrument 50 and/or the robotic arm 100. In other words, the virtual RCM as determined by the tracking method of the present disclosure is incorporated into the inverse kinematics calculations, constraining the movement of the robotic arm 100 relative to the access port 55 without physical constraints imposed by the port latch 46*c*.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:

a robotic arm including a plurality of joints;

an access port disposed in a patient body wall through an incision point and decoupled from the robotic arm;

an instrument coupled to the robotic arm and configured to be inserted into the access port;

a surgeon console including a handle controller configured to receive user input for moving the instrument and the robotic arm; and a controller configured to:

move at least one of the instrument or the robotic arm in response to the user input;

monitor torque associated with the robotic arm during the moving;

estimate a position of the access port or the incision point based on the monitored torque and gradually refine the estimate during the moving;

calculate at least one force applied against the patient body wall based on the monitored torque; and maintain a remote center of motion which aligns with the incision point during the moving based on the estimate, of at least one of the instrument or the robotic arm, wherein the controller controls the moving to reduce the calculated at least one force applied against the patient body wall.

2. The surgical robotic system according to claim 1, further comprising:

an instrument drive unit coupled to the robotic arm and configured to actuate the instrument.

3. The surgical robotic system according to claim 1, further comprising:

a camera configured to capture video of the robotic arm, wherein the controller is further configured to determine a position of at least one joint of the plurality of joints based on the video.

4. The surgical robotic system according to claim 3, wherein each joint of the plurality of joints includes a marker detectable by the camera.

5. The surgical robotic system according to claim 1, further comprising:

an endoscope camera coupled to the robotic arm, wherein the endoscope camera is configured to capture video of the access port and the controller is further configured to determine a position of the access port based on the video.

6. The surgical robotic system according to claim 5, wherein the access port includes a marker detectable by the endoscope camera.

7. The surgical robotic system according to claim 1, further comprising:

at least one electromagnetic tracker disposed on at least one of the access port, the instrument, or the robotic arm; and an electromagnetic emission detector configured to monitor electromagnetic emission of the at least one electromagnetic tracker and to determine position of the at least one electromagnetic tracker based on the electromagnetic emission.

8. The surgical robotic system according to claim 7, wherein the controller is further configured to maintain the remote center of motion which aligns with the incision point while moving at least one of the instrument or the robotic arm based on the position of the at least one electromagnetic tracker.

9. A surgical robotic system comprising:

a robotic arm including a plurality of joints;

an access port disposed in a patient body wall through an incision point and decoupled from the robotic arm; and a controller configured to:

move the robotic arm;

monitor torque associated with the robotic arm during the moving of the robotic arm;

estimate a position of the access port or the incision point based on the monitored torque and gradually refine the estimate during the moving of the robotic arm;

calculate at least one force applied against the patient body wall based on the monitored torque; and maintain a remote center of motion which aligns with the incision point during the moving of the robotic arm based on the estimate, of the robotic arm, wherein the controller controls the moving of the robotic arm to reduce the calculated at least one force applied against the patient body wall.

10. The surgical robotic system according to claim 9, further comprising:

an instrument; and an instrument drive unit coupled to the robotic arm and configured to actuate the instrument.

11. The surgical robotic system according to claim 10, further comprising:

a surgeon console including a handle controller configured to receive user input for moving the instrument and the robotic arm.

12. The surgical robotic system according to claim 11, wherein the controller is further configured to maintain the remote center of motion while moving the instrument and the robotic arm.

13. The surgical robotic system according to claim 9, further comprising:

a camera configured to capture video of the robotic arm, wherein the controller is further configured to determine a position of at least one joint of the plurality of joints based on the video.

14. The surgical robotic system according to claim 13, wherein each joint of the plurality of joints includes a marker detectable by the camera.

15. The surgical robotic system according to claim 9, further comprising:

an endoscope camera coupled to the robotic arm, wherein the endoscope camera is configured to capture video of the access port and the controller is further configured to determine a position of the access port based on the video.

16. The surgical robotic system according to claim 15, wherein the access port includes a marker detectable by the endoscope camera.

17. A method for controlling a surgical robotic system, the method comprising:

receiving user input at a surgeon console including a handle controller configured to receive the user input;

moving at least one of an instrument or a robotic arm in response to the user input, wherein the instrument is inserted through an access port disposed in a patient body wall through an incision point and decoupled from the robotic arm and the robotic arm includes a plurality of joints;

monitoring torque associated with the robotic arm during the moving;

estimating a position of the access port or the incision point based on the monitored torque and gradually refine the estimate during the moving;

calculating at least one force applied against the patient body wall based on the monitored torque; and maintaining a remote center of motion which aligns with the incision point during the moving based on the estimate, of at least one of the instrument or the robotic arm, wherein the moving is controlled to reduce the calculated at least one force applied against the patient body wall.

18. The method according to claim 17, further comprising:

capturing video of the robotic arm at a video camera; and determining a position of at least one joint of the plurality of joints based on the video.

19. The method according to claim 17, further comprising:

capturing video of the access port at an endoscope camera coupled to the robotic arm; and determining a position of the access port based on the video.

20. The method according to claim 17, further comprising:

monitoring electromagnetic emission of at least one electromagnetic tracker disposed on at least one of the access port, the instrument, or the robotic arm;

determining a position of the at least one electromagnetic tracker an electromagnetic emission detector; and determining a position of at least one of the access port, the instrument, or the robotic arm based on the position of the at least one electromagnetic tracker.

* * * * *